US007655253B2

(12) United States Patent
Kuenen et al.

(10) Patent No.: US 7,655,253 B2
(45) Date of Patent: Feb. 2, 2010

(54) NAVEL ORANGEWORM PHEROMONE COMPOSITION

(75) Inventors: Lodewyk P. S. Kuenen, Squaw Valley, CA (US); Walter S. Leal, Davis, CA (US); Jocelyn G. Millar, Riverside, CA (US); Douglas J. Pesak, Oxford, CT (US); Ana Lia Parra Pedrazzoli, Piracicaba (BR); Frank G. Zalom, Davis, CA (US)

(73) Assignees: Bedoukian Research, Inc., Danbury, CT (US); The Regents of the University of California, Oakland, CA (US); The United States of America Secretary of Agriculture, Washington, DC (US)

( * ) Notice: Subject to any disclaimer, the term of this patent is extended or adjusted under 35 U.S.C. 154(b) by 520 days.

(21) Appl. No.: 11/339,088

(22) Filed: Jan. 24, 2006

(65) Prior Publication Data

US 2006/0280765 A1 Dec. 14, 2006

Related U.S. Application Data

(63) Continuation-in-part of application No. 10/997,503, filed on Nov. 24, 2004, now abandoned.

(51) Int. Cl.
*A01N 25/00* (2006.01)
(52) U.S. Cl. .................. 424/405; 514/549; 514/703; 514/762; 554/223; 585/16
(58) Field of Classification Search ................ 424/405; 514/549, 703, 762; 554/223; 585/16
See application file for complete search history.

(56) References Cited

OTHER PUBLICATIONS

Sonnet PE, Heath RR. "Stereospecific synthesis of (Z,Z)-11,13-hexadecadienal, a female sex pheromone of the navel orangeworm, *Amyelois transitella* (Lepidoptera: Pyralidae)" (1980) J Chem Ecol 6:221-228.

Svirskaya PI, Maiti SN, Jones AJ, Khouw B, Leznoff CC.; "Syntheses of pure (9Z,11Z), (9E,11E), (9E,11Z), and (9Z,11E)-9,11-hexadecadienals—Possible candidate pheromones" (1984) J Chem Ecol 10:795-807.

Ando T, Inomata SI, Yamamoto M "Lepidopteran sex pheromones" (2004). Top Curr Chem 239:51-96.

Coffelt, J.A. et al., Isolation, Identification, and Synthesis of a Female Sex Pheremone of the Navel Orangeworm, *Amyelois transitella* (Lepidopera: Pyralidae), Journal of Chemical Ecology, vol. 5, No. 6, 1979, 955-966.

Curtis CE, Clark JD. Pheromone application and monitoring equipment used in field studies of the navel orangeworm (Lepidoptera: Pyralidae) (1984) J Econ Entomol 77:1057-1061.

Curtis CE, Landolt PJ, Clark JD "Disruption of navel orangeworm (Lepidoptera: Pyralidae) mating in large-scale plots with synthetic sex pheromone" (1985) J Econ Entomol 78:1425-1430.

(Continued)

*Primary Examiner*—Deborah D Carr
(74) *Attorney, Agent, or Firm*—Townsend and Townsend and Crew LLP (57) ABSTRACT

The present invention provides compounds useful for preparing synthetic pheromone compositions that can be used as attractants or inhibitors of insect species. The compositions are useful in the control of navel orangeworm or meal moth insect pests.

8 Claims, 6 Drawing Sheets

OTHER PUBLICATIONS

Jurenka R. "Insect pheromone biosysnthesis" (2004) Top Curr Chem 239:97-132.

Landolt PJ, Curtis CE "Interspecific sexual attraction between *Pyralis farinalis* L. and *Amyelois transitella* (Walker) (Lepidoptera: Pyralidae)" (1982) J Kansas Entomol Soc 55:248-252.

Shorey HH, Gerber RG. "Use of puffers for disruption of sex pheromone communication among navel orangeworm moths (Lepidoptera: Pyralidae) in almonds, pistachios, and walnuts" (1996) Environ Entomol 25:1154-1157.

Landolt PJ, Curtis CE, Coffelt JA, Vick KW, Sonnet PE, Doolittle RE. "Disruption of mating in the navel orangeworm with (Z,Z)-11,13-hexadecadienal" (1981). Environ Entomol 10:745-750.

NAVEL ORANGEWORM PHEROMONE COMPOSITION

CROSS-REFERENCES TO RELATED APPLICATIONS

Not Applicable

STATEMENT AS TO RIGHTS TO INVENTIONS MADE UNDER FEDERALLY SPONSORED RESEARCH OR DEVELOPMENT

Not Applicable

BACKGROUND OF THE INVENTION

Female-produced sex pheromones in moths (Lepidoptera) are normally complex mixtures of straight chain acetates, aldehydes, and alcohols, with 10-18 carbon atoms and up to three unsaturations. This group of pheromones, Type I according to Ando's classification (Ando et al., *Top Curr Chem* 239:51-96 (2004)) comprises ca. 75% of the known pheromones. A second major group, Type II (15%) (Ando et al., *Top Curr Chem* 239:51-96 (2004)) consists of polyunsaturated (up to four double bonds) hydrocarbons and epoxy derivatives with long straight chain ($C_{17}$-$C_{23}$) (Ando et al., *Top Curr Chem* 239:51-96 (2004)). While Type I pheromones are synthesized de novo (Ando et al., *Top Curr Chem* 239:51-96 (2004); Jurenka, R., *Top Curr Chem* 239:97-132 (2004)), polyunsaturated hydrocarbons seem to be derived from dietary linoleic and linolenic acid (Jurenka, R., *Top Curr Chem* 239:97-132 (2004); Ando et al., *Top Curr Chem* 239:51-96 (2004)).

The major constituent of the sex pheromones of two species in the family Pyralidae, the navel orangeworm, *Amyelois transitella* Walker (subfamily: Phycitinae) (Coffelt et al., *J Chem Ecol* 5:955-966 (1979)) and the meal moth, *Pyralis farinalis* Linnaeus (subfamily: Pyralinae) (Landolt, P. J. and Curtis, C. E., *J Kansas Entomol Soc* 55:248-252 (1982)) has been previously identified as (Z,Z)-11,13-hexadecadienal belonging to Type I (Ando et al., *Top Curr Chem* 239:51-96 (2004)). It has been suggested that additional pheromone components may be present in the female navel orangeworm moths (Shorey, H H., Gerber, R. G., *Environ Entomol* 25:1154-1157 (1996)), but hitherto conventional approaches have failed to identify the full pheromone system. The present invention addresses these and other needs.

BRIEF SUMMARY OF THE INVENTION

The present invention provides a new synthetic pheromone composition comprising Z,Z-11,13-hexadecadienal, and at least one of the following compounds (Z,Z,Z,Z,Z)-3,6,9,12,15-tricosapentaene, (Z,Z,Z,Z,Z)-3,6,9,12,15-pentacosapentaene, (Z,Z)-11,13-hexadecadienoate, and Z,Z-11,13-hexadecadien-1-ol.

In some embodiments, the present invention provides a new synthetic pheromone composition comprising Z,Z-11,13-hexadecadienal, and (Z,Z,Z,Z,Z)-3,6,9,12,15-tricosapentaene. The composition may further comprise (Z,Z,Z,Z,Z)-3,6,9,12,15-pentacosapentaene. In further embodiments, the synthetic pheromone composition also comprises Z,Z-11,13-hexadecadien-1-ol. In still other embodiments, the synthetic pheromone composition also comprises at least one member selected from the group consisting of Z,E-11,13-hexadecadienal, E,Z-11,13-hexadecadienal, Z-11-hexadecenal, hexadecanal, Z,E-11,13-hexadecadien-1-ol, Z-11-hexadecen-1-ol and methyl hexadecanoate.

In another embodiment, the synthetic pheromone composition comprises Z,Z-11,13-hexadecadienal, (Z,Z,Z,Z,Z)-3,6,9,12,15-tricosapentaene and ethyl (Z,Z)-11,13-hexadecadienoate. The composition may further comprise (Z,Z,Z,Z,Z)-3,6,9,12,15-pentacosapentaene. In still another embodiment, the synthetic pheromone composition also comprises at least one member selected from the group consisting of Z-13-hexadecenal and ethyl palmitate.

In other embodiments, the synthetic pheromone composition also comprises at least one member selected from the group consisting of (Z,Z)-11,13-hexadecadien-1-yl acetate and hexadecyl acetate.

In a further embodiment, the present invention provides an isolated compound selected from the group consisting of (Z,Z,Z,Z,Z)-3,6,9,12,15-tricosapentaene and (Z,Z,Z,Z,Z)-3,6,9,12,15-pentacosapentaene. In another embodiment, the present invention provides the isolated compound ethyl (Z,Z)-11,13-hexadecadienoate.

In another embodiment, the present invention provides an insect pest trap comprising a trap and the synthetic pheromone compositions of the invention In other embodiments, the present invention provides a method for attracting an insect pest using an insect pest trap comprising a trap and a synthetic pheromone composition of the invention.

BRIEF DESCRIPTION OF THE DRAWINGS

FIG. 3. Captures of the navel orangeworm and meal moth in traps baited with virgin females of the navel orangeworm and synthetic pheromone mixtures. (A) Catches of male navel orangeworm in traps baited with the previously identified constituent (ALD), full pheromone mixture and virgin female. (B) Catches of the meal moth in Davis, CA in traps baited with virgin females of the navel orangeworm and pheromone mixtures. Note that catches of the meal moth in traps baited with virgin females of the navel orangeworm are completely shut off by the addition of 4, (Z,Z)-11,13-hexadecadien-1-yl acetate. Captures in traps loaded with the synthetic mixture devoid of 4 were significantly higher than in traps baited with virgin females of the navel orangeworm, indicating that the natural behavioral antagonist fends off the male meal moth.

DETAILED DESCRIPTION OF THE INVENTION

I. Definitions

As used herein, the term "attracting" refers to the action of causing an insect pest, either directly or indirectly, to move in a direction towards the source of stimulus. One of skill in the art will recognize that suitable stimuli include thermostimuli, mechanostimuli, for example, airborne sound waves, or substrate borne pressure waves, electromagnetic stimulus including visual stimulus such as patterns, objects, color, light, and chemical stimulus including pheromones. A chemical stimulus can be an individual compound or a composition, including more than one compound, that either directly or indirectly, causes the insect to move toward the source of the stimulus.

As used herein, the term "inhibiting" refers to the action of causing an insect pest, either directly or indirectly, to not move in a direction towards the source of stimulus. One of skill in the art will recognize that suitable stimuli include thermostimuli, mechanostimuli, for example, airborne sound waves, or substrate borne pressure waves, electromagnetic stimulus including visual stimulus such as patterns, objects, color, light, and chemical stimulus including pheromones. A chemical stimulus can be an individual compound or a composition, including more than one compound, that either directly or indirectly, causes the insect to fail to move in a direction toward the source of the stimulus. Useful stimuli include those that also repel, or drive away, insect pests of the present invention.

As used herein, the term "insect pest" refers to any insect that is disruptive or destructive to the growth and development of agricultural crops. Examples of agricultural crops useful in the present invention include, but are not limited to, almonds, walnuts and pistachios. In some embodiments, insect pests of the present invention belong to the family Pyralidae. In other embodiments, insect pests of the present invention belong to the subfamily Phycitinae or Pyralinae. In still other embodiments, insect pests of the present invention include the navel orangeworm, *Amyelois transitella* Walker, and the meal moth, *Pyralis farinalis* Linnaeus. One of skill in the art will recognize that further insect pests will be useful in the present invention.

As used herein, the term "isolated" refers to a substance that has been separated from one or more substances so as to obtain pure or in a free state. In some embodiments, methods of isolation include crystallization and chromatography. Other methods of isolation will be apparent to one of skill in the art.

As used herein, the term "synthetic pheromone composition" refers to a chemical composition of one or more specific isolated pheromone compounds. Typically, such compounds are produced synthetically and mimic the response of natural pheromones. Pheromones are compounds produced by an animal or insect and serve as a stimulus to other individuals of the same species for one or more behavioral responses. In some embodiments, the behavioral response to the pheromone is attraction. In other embodiments, the species to be influenced is repelled by the pheromone. In these embodiments, the pheromone is an inhibitor.

As used herein, the term "trap" refers to any device into which the synthetic pheromone compositions of the present invention are placed, and that prevents the insect pest from escaping once the insect pest has come into contact with the trap. The present invention provides traps that can be of various sizes, shapes, colors, and materials. Traps of the present invention can be designed and manufactured specifically for use as an insect trap, or can be a container converted and adapted from other uses such as, for example, a glass Petri dish, a metal coffee can, a cardboard box, or any ordinary plastic, metal, fiberglass, composite or ceramic container. Preferred materials for use in making the traps of the present invention include, but are not limited to, cardboard, metal, metal alloys, glass, paper, plastic, acrylic, fiberglass, composite, and ceramic. The traps of the present invention preferably have a bottom, sidewalls, and a top. The bottom, sidewalls and top of the trap can be solid, or be perforated. An example of a perforated sidewall is a screen. The traps are configured such that insect pests can enter the trap but are unable to escape once inside the trap. Other useful traps of the present invention are commercially available (for example, from Trece Inc.).

As used herein, the term "mating disruption" refers to the release of synthetic pheromone compositions (e.g., using controlled release from polymers comprising the pheromone, or by automated aerosol dispensers) in sufficient quantities that males are unable to orient to natural sources of pheromone, fail to locate females, and reproduction is thus prevented.

II. Compounds

The compounds of the present invention are useful for preparing synthetic pheromone compositions that can be used as attractants or inhibitors of insect species. Use of synthetic pheromone compositions for control insect pests is well known in the art. One of skill in the art can conveniently use the compounds of the invention in the preparation of synthetic pheromone compositions useful in a variety of contexts. Exemplary methods for preparing the compounds of the present invention are described in the Examples section below.

In one embodiment, the present invention provides an isolated compound selected from the group consisting of ethyl (Z,Z)-11,13-hexadecadienoate, (Z,Z,Z,Z,Z)-3,6,9,12,15-tricosapentaene and (Z,Z,Z,Z,Z)-3,6,9,12,15-pentacosapentaene. Additional compounds useful in the present invention include, but are not limited to, Z,Z-11,13-hexadecadienal, Z,Z-11,13-hexadecadien-1-ol, Z,E-11,13-hexadecadienal, E,Z-11,13-hexadecadienal, Z-11-hexadecenal, hexadecanal, Z,E-11,13-hexadecadien-1-ol, Z-11-hexadecen-1-ol and methyl hexadecanoate. Other compounds useful in the present invention include Z-13-hexadecenal and ethyl palmitate. Further compounds useful in the present invention include (Z,Z)-11,13-hexadecadien-1-yl acetate and hexadecyl acetate.

III. Synthetic Pheromone Compositions

The synthetic pheromone compositions of the present invention are useful for attracting, inhibiting or controlling a number of insect pests. As explained in detail below, the compositions are conveniently used for control of the navel orangeworm and the meal moth. In some embodiments, the synthetic pheromone compositions of the present invention are useful for inhibiting the meal moth.

Synthetic pheromone compositions can be conveniently tested in the assays described below. For example, the synthetic pheromone compositions of the present invention can be tested to determine affinity for a pheromone-binding protein (AtraPBP) present in the navel orangeworm. Alternatively, the compositions can be tested for the ability to stimulate the olfactory receptor neurons (ORNs) in the insect's sensilla trichodea producing a response that indicates the presence or absence of a pheromone. In a typical embodiment, the compositions stimulate an electroantennogram response from an insect pest antenna, as described below.

A synthetic pheromone composition of the invention comprises one or more of the isolated compounds disclosed here. For example, a synthetic pheromone composition useful in the present invention comprises Z,Z-11,13-hexadecadienal and one or more of the following compounds: (Z,Z,Z,Z,Z)-3,6,9,12,15-tricosapentaene, (Z,Z,Z,Z,Z)-3,6,9,12,15-pentacosapentaene Z,Z-11,13-hexadecadien-1-ol, and (Z,Z)-11,13-hexadecadienoate.

A typical synthetic pheromone composition useful in the present invention comprises Z,Z-11,13-hexadecadienal and (Z,Z,Z,Z,Z)-3,6,9,12,15-tricosapentaene. It may further comprise (Z,Z,Z,Z,Z)-3,6,9,12,15-pentacosapentaene.

Additional synthetic pheromone compositions of the present invention also comprises a member selected from the group consisting of Z,Z-11,13-hexadecadien-1-ol, Z,E-11,13-hexadecadienal, E,Z-11,13-hexadecadienal, Z-11-hexadecenal, hexadecanal, Z,E-11,13-hexadecadien-1-ol, Z-11-hexadecen-1-ol and methyl hexadecanoate.

Other synthetic pheromone compositions of the present invention comprise Z,Z-11,13-hexadecadienal, (Z,Z,Z,Z,Z)-3,6,9,12,15-tricosapentaene (Z,Z)-11,13-hexadecadienoate, Z-13-hexadecenal and ethyl palmitate.

Further compounds useful in the synthetic pheromone compositions of the present invention include (Z,Z)-11,13-hexadecadien-1-yl acetate and hexadecyl acetate.

In some embodiments, the present invention provides a synthetic pheromone composition comprising (Z,Z,Z,Z,Z)-3,6,9,12,15-tricosapentaene, (Z,Z,Z,Z,Z)-3,6,9,12,15-pentacosapentaene, (Z,Z)-11,13-hexadecadienal, ethyl palmitate and ethyl (Z,Z)-11,13-hexadecadienoate. Such synthetic pheromone compositions are useful, for example, in attracting or controlling the navel orangeworm and meal moth.

In other embodiments, the present invention provides a synthetic pheromone composition comprising (Z,Z,Z,Z,Z)-3,6,9,12,15-tricosapentaene, (Z,Z,Z,Z,Z)-3,6,9,12,15-pentacosapentaene, (Z,Z)-11,13-hexadecadienal, ethyl palmitate, ethyl (Z,Z)-11,13-hexadecadienoate and (Z,Z)-11,13-hexadecadien-1-yl acetate. Such synthetic pheromone compositions are useful, for example, in attracting the navel orangeworm and repelling the meal moth. These compositions contain an antagonist of the meal moth, which operates to inhibit the meal moth.

The particular ratio of the compounds in the synthetic pheromone compositions of the invention is not a critical aspect of the invention. For example, the present invention provides a synthetic pheromone composition comprising compounds in about the following ratio: (Z,Z,Z,Z,Z)-3,6,9,12,15-tricosapentaene, 1-40; (Z,Z,Z,Z,Z)-3,6,9,12,15-pentacosapentaene, 1-50; (Z,Z)-11,13-hexadecadienal, 100; ethyl palmitate, 0-15; ethyl (Z,Z)-11,13-hexadecadienoate, 0-10; and (Z,Z)-11,13-hexadecadien-1-yl acetate, 0-10. A preferred composition comprises the compounds in about the following ratio: (Z,Z,Z,Z,Z)-3,6,9,12,15-tricosapentaene, 15; (Z,Z,Z,Z,Z)-3,6,9,12,15-pentacosapentaene, 17; (Z,Z)-11,13-hexadecadienal, 100; ethyl palmitate, 14; ethyl (Z,Z)-11,13-hexadecadienoate, 5; and (Z,Z)-11,13-hexadecadien-1-yl acetate, 5. One of skill in the art will recognize that other similar ratios of compounds for the synthetic pheromone compositions of the present invention are also useful.

IV. Insect Pest Traps

The present invention also provides an insect pest trap comprising a synthetic pheromone composition of the invention. An insect pest trap of the invention comprises one or more of the isolated compounds disclosed here. For example, an insect pest trap useful in the present invention comprises Z,Z-11,13-hexadecadienal and (Z,Z,Z,Z,Z)-3,6,9,12,15-tricosapentaene. They may further comprise (Z,Z,Z,Z,Z)-3,6,9,12,15-pentacosapentaene.

Additional insect pest traps of the present invention also comprises a member selected from the group consisting of Z,Z-11,13-hexadecadien-1-ol, Z,E-11,13-hexadecadienal, E,Z-11,13-hexadecadienal, Z-11-hexadecenal, hexadecanal, Z,E-11,13-hexadecadien-1-ol, Z-11-hexadecen-1-ol and methyl hexadecanoate.

Other insect pest traps of the present invention comprise Z,Z-11,13-hexadecadienal and (Z,Z,Z,Z,Z)-3,6,9,12,15-tricosapentaene, (Z,Z)-11,13-hexadecadienoate, Z-13-hexadecenal and ethyl palmitate.

Further compounds useful in the insect pest traps of the present invention include (Z,Z)-11,13-hexadecadien-1-yl acetate and hexadecyl acetate.

In one embodiment, the present invention provides an insect pest trap wherein the synthetic pheromone composition comprises (Z,Z,Z,Z,Z)-3,6,9,12,15-tricosapentaene and (Z,Z,Z,Z,Z)-3,6,9,12,15-pentacosapentaene. In another embodiment, the present invention provides an insect pest trap wherein the synthetic pheromone composition comprises (Z,Z,Z,Z,Z)-3,6,9,12,15-tricosapentaene, (Z,Z,Z,Z,Z)-3,6,9,12,15-pentacosapentaene, (Z,Z)-11,13-hexadecadienal, ethyl palmitate and ethyl (Z,Z)-11,13-hexadecadienoate. In still another embodiment, the present invention provides an insect pest trap wherein the synthetic pheromone composition comprises (Z,Z,Z,Z,Z)-3,6,9,12,15-tricosapentaene, (Z,Z,Z,Z,Z)-3,6,9,12,15-pentacosapentaene, (Z,Z)-11,13-hexadecadienal, ethyl palmitate, ethyl (Z,Z)-11,13-hexadecadienoate and (Z,Z)-11,13-hexadecadien-1-yl acetate.

In other embodiments, the synthetic pheromone composition of the present invention is formulated in rubber septa or in disks. One of skill in the art will recognize that other formulations are useful in the present invention.

V. Methods for Attracting an Insect Pest

The present invention also provides an method for attracting an insect pest comprising a synthetic pheromone composition of the invention. The method for attracting an insect pest of the present invention comprises one or more of the isolated compounds disclosed here. For example, an method for attracting an insect pest useful in the present invention comprises Z,Z-11,13-hexadecadienal and (Z,Z,Z,Z,Z)-3,6,9,12,15-tricosapentaene. The methods of the present invention may further comprise (Z,Z,Z,Z,Z)-3,6,9,12,15-pentacosapentaene.

Additional methods for attracting an insect pests of the present invention also comprise a member selected from the group consisting of Z,Z-11,13-hexadecadien-1-ol, Z,E-11,13-hexadecadienal, E,Z-11,13-hexadecadienal, Z-11-hexadecenal, hexadecanal, Z,E-11,13-hexadecadien-1-ol, Z-11-hexadecen-1-ol and methyl hexadecanoate.

Other method for attracting an insect pest of the present invention also comprises (Z,Z)-11,13-hexadecadienoate, Z-13-hexadecenal and ethyl palmitate.

The present invention further provides a method for attracting an insect pest using an insect pest trap comprising a trap and a synthetic pheromone composition comprising (Z,Z,Z,Z,Z)-3,6,9,12,15-tricosapentaene, (Z,Z,Z,Z,Z)-3,6,9,12,15-pentacosapentaene, (Z,Z)-11,13-hexadecadienal, ethyl palmitate and ethyl (Z,Z)-11,13-hexadecadienoate. In another embodiment, the method for attracting an insect pest comprises a synthetic pheromone composition comprising (Z,Z,Z,Z,Z)-3,6,9,12,15-tricosapentaene, (Z,Z,Z,Z,Z)-3,6,9, 12,15-pentacosapentaene, (Z,Z)-11,13-hexadecadienal, ethyl palmitate, ethyl (Z,Z)-11,13-hexadecadienoate and (Z,Z)-11,13-hexadecadien-1-yl acetate.

One of skill will recognize that the manner in which the pest traps of the invention are used will depend upon the particular pest to be controlled or crop to be protected. In some embodiments, the insect pest is from the species family Pyralidae. In preferred embodiments, the method is used for attracting or repelling an insect pest from the subfamily of Phycitinae or Pyralinae.

In a typical embodiment, the present invention provides a method for controlling an insect pest from the subfamily Phycitinae. In another embodiment, the present invention provides a method for attracting an insect pest such as the navel orangeworm, *Amyelois transitella* Walker.

In still other embodiments, the present invention provides a method for attracting an insect pest from the subfamily Pyralinae. In another embodiment, the present invention provides a method for attracting an insect pest such as the meal moth, *Pyralis farinalis* Linnaeus.

VI. Methods of Disrupting Mating

Use of synthetic pheromone compositions to disrupt mating of insect pests is well known in the art. Release of high and uniform concentrations of the pheromone are thought to shut down the ability of male sensory organs to detect the pheromone. In addition, if the pheromones are released from many sources males are attracted to false sources, wasting time and energy. Under these conditions, the likelihood of a male finding a female is reduced.

A number of devices that provide a synthetic pheromone reservoir and controlled release of the contents are known. For example, a common method relies upon evaporation from polymers impregnated or filled with pheromone. Such devices are typically composed of rubber and plastic in sizes ranging from sprayed microcapsules to long strips hung on trees. Such devices can be open-ended hollow fibers or hollow tubes having their lumen filled with the composition and sealed at the end. In addition, automated aerosol dispensers can be used.

Devices for the disruption of insect pest mating comprise one or more of the isolated compounds disclosed here. For example, a disruption device useful in the present invention comprises Z,Z-11,13-hexadecadienal and (Z,Z,Z,Z,Z)-3,6,9, 12,15-tricosapentaene. The device may further comprise (Z,Z,Z,Z,Z)-3,6,9,12,15-pentacosapentaene.

Additional disruption devices of the present invention also comprise a member selected from the group consisting of Z,Z-11,13-hexadecadien-1-ol, Z,E-11,13-hexadecadienal, E,Z-11,13-hexadecadienal, Z-11-hexadecenal, hexadecanal, Z,E-11,13-hexadecadien-1-ol, Z-11-hexadecen-1-ol and methyl hexadecanoate.

Other disruption devices of the present invention comprise Z,Z-11,13-hexadecadienal, (Z,Z,Z,Z,Z)-3,6,9,12,15-tricosapentaene (Z,Z)-11,13-hexadecadienoate, Z-13-hexadecenal and ethyl palmitate.

Further compounds useful in the disruption devices of the present invention include (Z,Z)-11,13-hexadecadien-1-yl acetate and hexadecyl acetate.

VII. EXAMPLES

General. Gas chromatography-mass spectrometry (GC-MS), described in Examples 1-6, was obtained with a 5973 Network Mass Selective Detector linked to a 6890 Network GC System (Agilent Technologies, Palo Alto, Calif.) operated either in the electron impact (EI) or chemical ionization (CI) mode. Chromatographic resolution was done on an HP-5MS column (30 m×0.25 mm; 0.25 µm; Agilent) that was operated at 70° C. for 1 min, increased to 250° C. at a rate of 10° C./min and held at this temperature for 10 min. Vapor phase infrared spectroscopy was carried out on a Win GC/IR Pro (Varian Inc., formerly Digilab, Randolph, Mass.) with a GC/IR interface and a Scimitar FTS 2000 linked to a 6890 Network GC System (Agilent). Separation was done on a HP-5 column (30 m×0.32 mm; 0.25 µm; Agilent) operated at 100° C. for 1 min, increased to 250° C. at a rate of 20° C./min and held at this temperature for 5 min; the transfer line and light pipe were operated at 250° C. Gas chromatography with electroantennographic detection (GC-EAD) was done with two different systems: HP 5890 and HP 6890 (Agilent) both having Syntech's GC-EAD transfer lines and temperature control units (Hilversum, The Netherlands). In both systems, the effluent from the capillary column was split into EAD and flame ionization detector (FID) in 3:1 ratios. Male antennae were placed in EAG probes (Syntech) and held in place with Spectra 360 electrode gel (Parker Laboratories, Orange, N.J.). These probes were connected to AM-01 amplifiers (Syntech). The analog signals were fed into A/D 35900E interfaces (Agilent) and acquired simultaneously with FID signal on an Agilent Chemstation. Chromatographic separations were done either with HP-5MS column operated as in GC-MS or with HP-INNOWAX column (30 m×0.32 mm; 0.25 µm; Agilent) operated at 70° C. for 1 min, increased to 250° C. at a rate of 10° C./min and held at this temperature for 5 min.

Example 1

Identification of Natural Pheromone Components

Insect rearing, pheromone extraction and fractionation. The navel orangeworm colony started from larvae collected in Bakersfield, Calif. The larvae were kept in dried and roasted pistachio at 25±2° C., 75±10% relative humidity, and a 16:8 (L:D) photoregime. Adults were transferred to aluminum cages (30×30×30 cm) and kept for 48 h to allow copulation. After the first generation, 20% of the emerged adults were used to maintain the colony. The remainder of the pupae were kept individually in culture tubes (17 mm i.d; 10 cm long). Upon emergence males were used for EAD and SSR and females for gland extracts or trap baits. Pheromone glands of 1- to 2-day-old virgin females were extracted 2 h before photophase for 10 min in glass-distilled hexane and kept at −80° C. until used. Crude extracts were subjected to flash column chromatography on silica gel (60-200 Mesh, Fisher Scientific) by successive elution with hexane-ether mixtures in the following order: 100:0 (hexane fraction), 99:1 (1% fraction), 98:2, 97:3, 95:5, 90:10, 50:50, 0:100.

Single sensillum recordings (SSR). Male moths were immobilized with dental wax on the recording stage of a single sensillum recording unit (Syntech, INR-02), the tip of the sensilla were cut (Kaissling, K. E. Single unit and electroantennogram recordings in insect olfactory organs, In: Spielman A. I., Brand J. G. (ed) *Experimental Cell Biology of Taste and Olfaction: Current Techniques and Protocols*, CRC Press, Boca Raton, pp.361-386 (1995)) and placed under a stereomicroscope (SZX12,Olympus, Tokyo, Japan). The indifferent (ground) electrode was a thin tungsten electrode inserted into the head. The recording glass electrode was slipped over the cut tip of the sensilla with a Piezo Manipulator (PM-10, World Precision Instruments, Sarasota, Fla.) while the signal was monitored with a Tektronix oscilloscope (TDS-2014). The pre-amplified signal was acquired with an acquisition system (IDAC-USB, Syntech) and SSR software (Autospike 2000, Syntech). The antennal preparation was continuously flushed with clean air at 0.5 m/s. Each stimulus was applied to a filter paper, dried at least 10 min, and placed within a glass cartridge (7 mm i.d.; 5 cm long). The cartridge opening was placed 1 cm in front of the antennae. The stimulus air was delivered by a stimulus controller (CD-02/E, Syntech).

Figure 1:
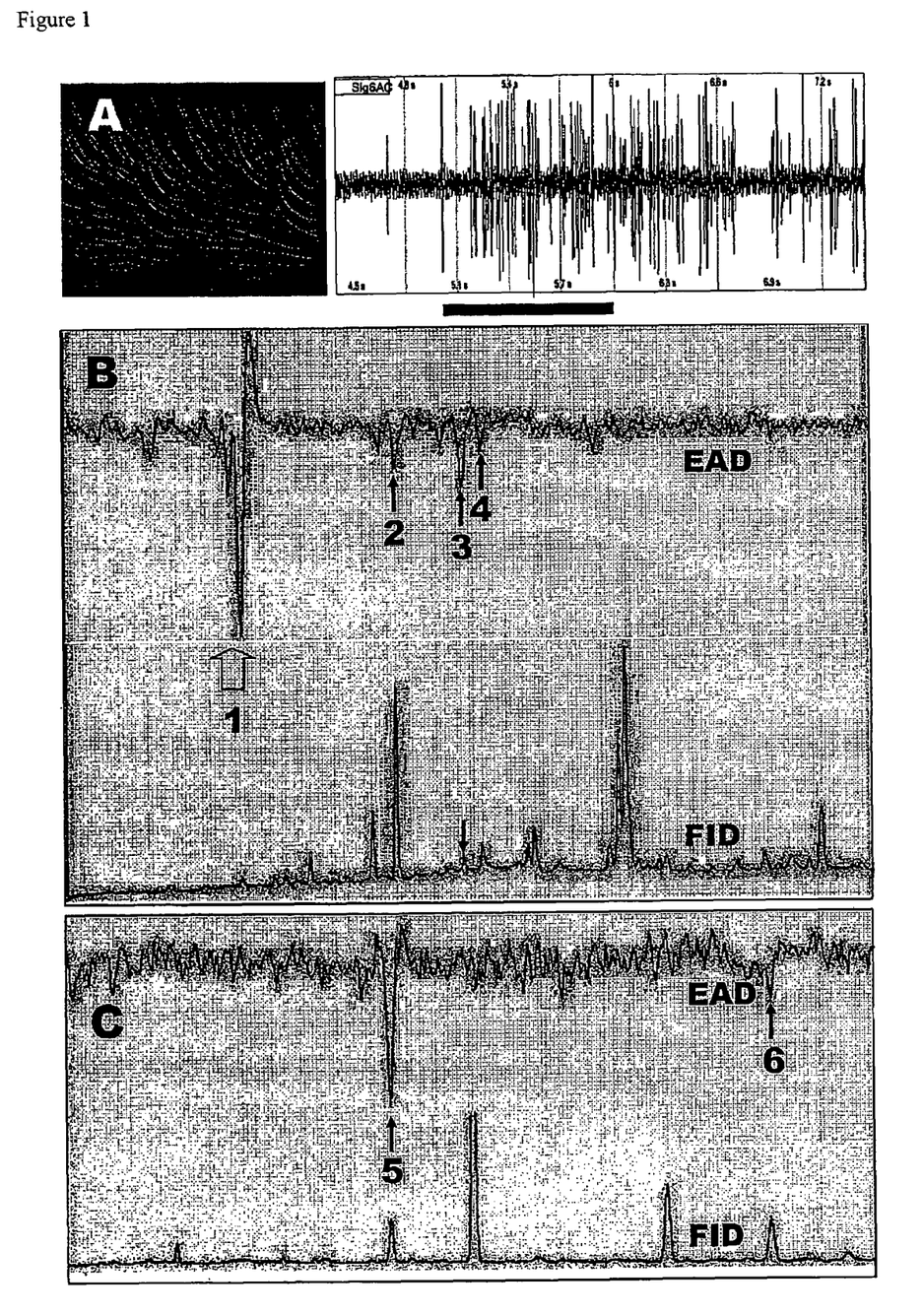
FIG. 1. (A) Left: Scanning electron micrograph (magnification, 300×) of a male antennae of the navel orange worm. Right: Electrophysiological recording from one of these sensilla trichodea stimulated by 5 female-equivalent of a gland extract. The bar represents the stimulus duration (1 s). GC-EAD recordings from the 3% (B) and hexane (C) fractions after separation of the crude extract by a silica gel column. The peaks highlighted (arrows) in the EAD traces were highly reproducible (N=20). Isomers of the known pheromone (Z,Z)-11,13-hexadecadienal (ALD) generated a cluster of peaks (open arrow).

Results. A comprehensive approach was taken in studying chemical communication in the navel orangeworm, *A. transitella*. Pheromone- and odorant-binding proteins were isolated, cloned, and expressed. Binding assays with recombinant olfactory proteins indicated that the previously identified pheromone, (ZZ)-11,13-hexadecadienal (ALD), bound to the major pheromone-binding protein (AtraPBP) with apparent high affinity. Preliminary screening of potential ligands showed that a related acetate compound, (Z,Z)-11,13-hexadecadienyl acetate, had similar affinity to AtraPBP. In addition, electrophysiological recordings from sensilla trichodea (single sensillum recordings, SSR) in male moth antennae indicated that the navel orangeworm possess multiple olfactory receptors neurons (ORN), which are stimulated by constituents in hexane extracts from pheromone glands (FIG. 1A).

The crude extract was fractionated by flash chromatography with electrophysiological activity being monitored by SSR. Different ORNs were stimulated not only by the ALD-containing fractions (5 and 10% ether), but also by two other fractions: hexane (0% ether) and 3% ether. Based on the spike amplitudes, it was not possible to conclude unambiguously whether different ORNs fired or if the SSR responses were derived only from minute amounts of ALD, particularly in the 3% fraction.

Gas chromatography coupled with an electroantennographic detector (GC-EAD) using male moth antennae as the sensing element was used to determine the active constituents in these SSR-active fractions (3% and hexane). GC-EAD analyses using a non-polar column (HP-5MS) indicated that in addition to the ALD pheromone (peak 1), the 3% fraction contained three other EAD-active peaks (2, 3, and 4) (FIG. 1B), whereas the hexane fraction contained two other EAD-active peaks (5 and 6) (FIG. 1C). The peaks were numbered in the order of their retention times ($t_R$) in a non-polar column (1: $t_R$, 17.30 min; 2: 18.44 min; 3: 18.96 min; 4: 19.08 min; 5: 20.9 min; 6: 23.8 min). The retention times of these EAD-active peaks in a polar column (HP-INNOWAX) were: 16.59, 17.37, 18.32, and 18.72 min (3% fraction) and 18.52 and 20.22 min (hexane fraction). GC-MS analyses indicated that the cluster of peaks (labeled peak 1 in FIG. 1B) is derived from the isomers of the previously identified pheromone, ALD.

Authentic synthetic standards showed the following order of elution by GC-MS: (Z,E)-, (E,Z)-, (Z,Z)-, and (E,E)-1 ($t_R$, 14.77, 14.86, 14.94, and 14.98 min, respectivley). The strongest EAD-active peak in the cluster (1) corresponds to the (Z,Z)-isomer, whereas the earlier eluting, small EAD-active peaks are generated by (Z,E)- and (E,Z)-isomers. While the occurrence in gland extracts of the major, (Z,Z)-, and other two minor isomers, i.e., (Z,E) and (E,Z), were clearly observed by both GC-EAD and GC-MS, the (E,E)-isomer was not detectable by these techniques. In SSR experiments, large spike amplitude cells (FIG. 1A) were activated by (Z,Z)-1, whereas synthetic (E,E)-1 activated mainly a small spike ORN, with small activation of a large spike cell.

Figure 2:
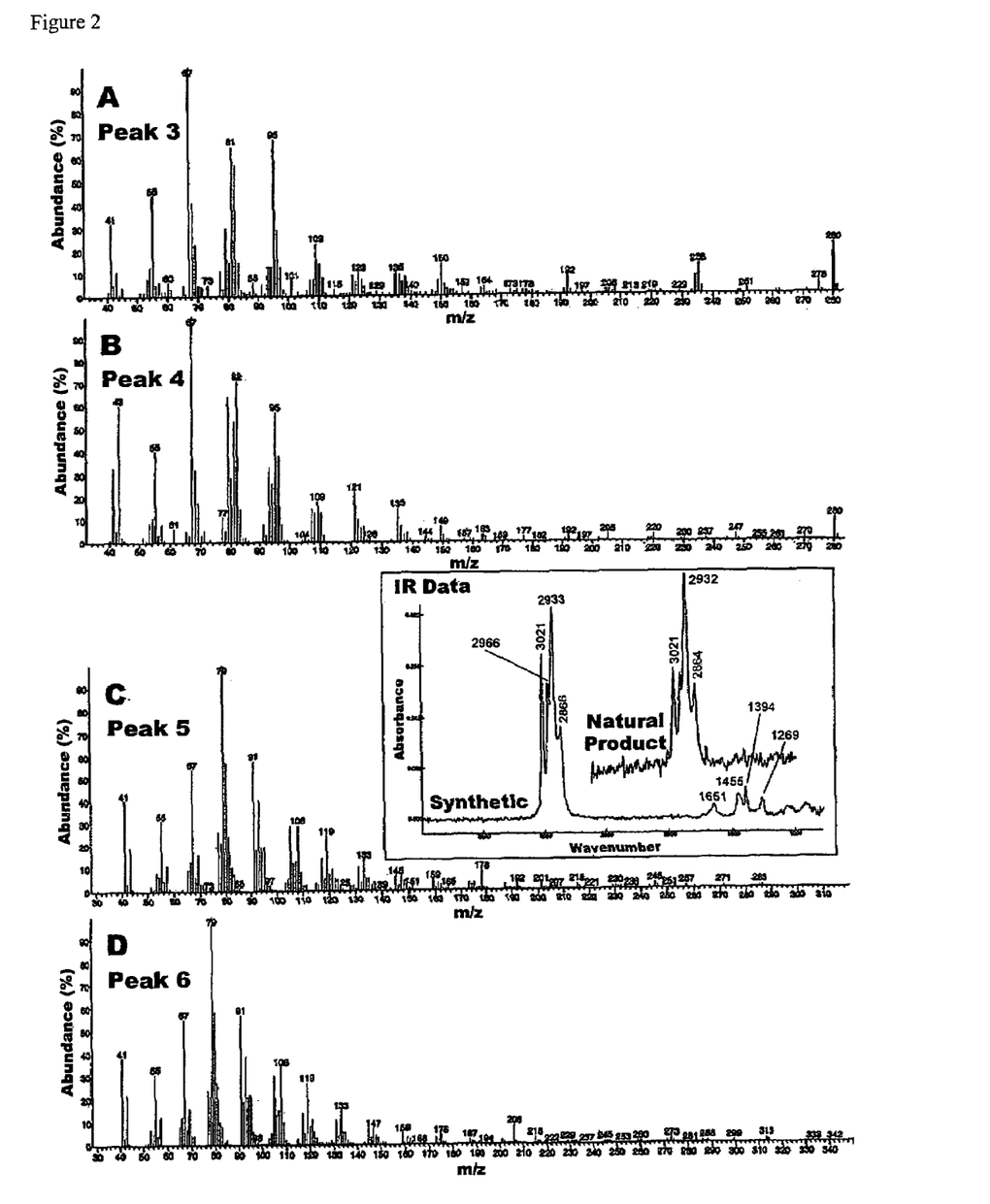
FIG. 2. MS and vapor-phase IR data of the novel natural products. (A): MS of ethyl (Z,Z)-11,13-hexadecadienoate. (B) MS of (Z,Z)-11,13-hexadecadien-1-yl acetate. (C) MS of (Z,Z,Z,Z,Z)-3,6,9,12,15-tricosapentaene; IR data of the synthetic and natural (inset) compound. (D) MS data of (Z,Z,Z,Z)-3,6,9,12,15-pentacosapentaene.

Peak 2 was identified as ethyl palmitate by GC-MS and library (Wiley) search. Co-elution with authentic ethyl palmitate (Aldrich) in polar and non-polar columns and EAD activity confirmed the identification. The fragmentation pattern in the MS of peak 3 (FIG. 2A) somewhat resembles that of the ALD constituent. The loss of 45 (molecular ion peak, m/z 280 and m/z 235) and the peak at m/z 88 suggested that 3 was a di-unsaturated ethyl ester. This assignment was also supported by the vapor phase infrared spectra with a strong carbonyl stretching band at 1753 $cm^{-1}$, as commonly observed in methyl and ethyl esters (Leal, W. S., Infrared and ultraviolet spectroscopy techniques; In: Millar J G, Haynes K F (ed) *Methods in Chemical Ecology: Chemical Methods*, Kluwer Academic Publishers, Norwell, pp. 185-206 (1998)). Although it was not possible to assign the location of the double bonds, it appeared on the basis of the MS profile that it might be derived from the same biosynthetic pathway as ALD and, therefore, having the double bonds in positions 11 and 13. Synthetic ethyl (Z,Z)-11,13-hexadecadienoate was indistinguishable from 3 in the MS and GC-IR profiles, retention times in polar and non-polar columns; synthetic 3 was also EAD active.

Peak 4 gave a MS (FIG. 2B) identical to that of synthetic (ZZ)-11,13-hexadecadien-1-yl acetate, utilized in molecular-based approach for screening of potential attractants (see above). Synthetic and natural compounds have identical retention times in polar and non-polar columns. Synthetic (Z,Z)-11,13-hexadecadien-1-yl acetate showed the same electrophysiological activity as the natural product. In summary the 3% fraction contained four EAD-active peaks, which were fully characterized as 1: (Z,Z)-11,13-hexadecadienal (CAS # 71317-73-2); 2: ethyl palmitate (CAS #628-97-7); 3: ethyl (Z,Z)-11,13-hexadecadienoate, and 4:(Z,Z)-11,13-hexadecadien-1-yl acetate (CAS #118744-50-6). Whereas mixtures of biosynthetically related aldehydes and acetates are commonly utilized in moth sex pheromones, this is the first identification of a novel ethyl ester likely derived from the same biosynthetic pathway as that of the major pheromone constituent (ALD).

MS data suggested that 5 and 6 were related compounds (FIG. 2 C, D). The base peak in the MS of 5 (FIG. 2C) appeared at m/z 79; chemical ionization (CI, methane) MS indicated that a tiny peak at m/z 314 was the molecular peak. CI gave two major peaks at m/z 313 ([M—H]$^+$) and 315 (base peak, [M+H]$^+$). Hydrogenation of the purified compound and MS analyses suggest that 5 is a pentaunsaturated straight chain hydrocarbon. The peak at m/z 1[Me(CH$_2$)$_6$(CH=CH)$_3$H]$^+$ suggest the occurrence of 6 methylenes after the last double bond (Karunen, P., Phytochemistry 13:2209-2213 (1974); Youngblood et al., *Marine Biol* 8:190-201 (1971); Lee et al., *Biochim Biophys Acta* 202:386-388 (1970); Blumer et al., *Marine Biol* 6:226-235 (1970)). The occurrence of a double bond in position 3 was inferred by the fragment [MeCH$_2$(CH=CH)$_3$H]$^+$ at m/z 108 (Karunen, P., Phytochemistry 13:2209-2213 (1974); Youngblood et al., Marine Biol 8:190-201 (1971); Lee et al., Biochim Biophys Acta 202:386-388 (Blumer et al., Marine Biol 6:226-235 (1970)) and the lack of vinyl $CH_2$ in vapor phase IR (Leal, W. S., Infrared and ultraviolet spectroscopy techniques; In: Millar J G, Haynes K F (ed) Methods in Chemical Ecology: Chemical Methods, Kluwer Academic Publishers, Norwell, pp. 185-206 (1998)) at ca. 3080 $cm^{-1}$ (FIG. 2C, inset). IR and MS suggest that there was no conjugation and the strong IR band at 3021 $cm^{-1}$ suggests that all double bonds had the cis configuration (Leal, W. S., Infrared and ultraviolet spectroscopy techniques; In: Millar J G, Haynes K F (ed) Methods in Chemical Ecology: Chemical Methods, Kluwer Academic Publishers, Norwell, pp. 185-206 (1998)) (FIG. 2C). MS of 6 showed evidence for 8 methylenes after the last double bond: m/z 206, $[Me(CH_2)_8(CH=CH)_3H]^+$. (Karunen, P., Phytochemistry 13:2209-2213 (1974); Youngblood et al., Marine Biol 8:190-201 (1971); Lee et al., Biochim Biophys Acta 202:386-388 (1970); Blumer et al., Marine Biol 6:226-235 (1970)) The molecular peak at m/z 342 was confirmed by CI. Like 5, compound 6 showed no band corresponding to vinyl $CH_2$ in vapor phase IR, no conjugation, and evidence for all-cis configuration. Thus, the two compounds were identified as (Z,Z,Z,Z,Z)-3,6,9,12,15-tricosapentaene and (Z,Z,Z,Z,Z)-3,6,9,12,15-pentacosapentaene, respectively. The synthetic polyunsaturated hydrocarbons were indistinguishable from the natural products in their MS, IR, and retention times under GC-EAD and GC-MS separation conditions. Even with a shallow separation method in a polar column (INNO-WAX; 70° C. to 250° C. at 5° C./min), both synthetic and natural products gave the same retention time: (Z,Z,Z,Z,Z,)-3,6,9,12,15-tricosapentaene, 31.33 min; (Z,Z,Z,Z,Z)-3,6,9,12,15-pentacosapentaene, 34.42 min.

The synthetic polyunsaturated hydrocarbons were also EAD-active. Hitherto monoene, diene, triene and tetraene hydrocarbons ($C_{17}$-$C_{23}$) have been identified as sex pheromones (Ando et al., Top Curr Chem 239:51-96 (2004)), but pentaenes are not known. Both 5 and 6 are novel types of natural products, but a shorter pentaene, (Z,Z,Z,Z,Z)-3,6,9,12,15-heneicosapentaene (CAS 66887-59-0), has been previously identified from marine benthic algae (Youngblood et al., Marine Biol 8:190-201 (1971)) and spores of a moss (Karunen, P., Phytochemistry 13:2209-2213 (1974)). Given the methylene-interrupted pattern of the 3,6,9 moiety, it is conceivable that these novel moth pheromones (5 and 6) could be derived from linolenic acid after chain elongation, desaturation and decarboxylation, provided the insect possesses the appropriate enzymes.

Example 2

(Z,E)-, (E,Z)-, (E,E)-, and (Z,Z)-11,13-Hexadecadienal (1)

The (Z,Z) isomer can be prepared by a previously published method (Sonnet, P. E. and Heath, R. R., J Chem Ecol 6:221-228 (1980). The (Z,E) isomer was prepared by a the sequence shown in Scheme 1-1. (E)-12-pentadecen-10-yn-1-ol THP was prepared by palladium catalyzed cross coupling of 10-undecyn-1-ol THP (prepared from 10-undecyn-1-ol and dihydropyran) with E-1-iodo-1-butene (Zweifel, G. and Whitney, C. C., J Am Chem Soc 89:2753-2754 (1967); Alami et al., Tetrahedron Lett 34:6403-6406 (1993)). Addition of dicyclohexyl borane across the triple bond followed by hydrolysis of both the borane and THP protecting group gave the desired (Z,E) diene stereochemistry (Brown, H. C., Organic Synthesis via Boranes, John Wiley and Sons, New York (1975)). The alcohol was converted to bromide via the mesylate using conventional methods (Jones, R. A., Quaternary ammonium salts, Academic Press.San Diego (2001)). The Grignard reagent of the bromide was then prepared and reacted with triethylorthoformate to give (Z,E)-11,13-Hexadecadienal diethyl acetal (DeWolfe, H. R., Carboxylic ortho acid derivatives, Academic Press. New York (1970)). Acidic hydrolysis (Greene T. W. and Wuts, P. G. M., Protective groups in organic synthesis, John Wiley & Sons.New York (1999)) gave the desired aldehyde. The (E,Z) isomer was prepared by the sequence shown in Scheme 1-2. (E)-10-pentadecen-12-yn-1-ol THP was prepared from the borane adduct of 10-undecyn-1-ol THP and the lithium salt of 1-butyne (Svirskaya et al., J Chem Ecol 10:795-807 (1984)). The rest of the synthesis follows that of the (Z,E) isomer from the THP stage described above. The (E,E) isomer was prepared by isomerization of the (Z,Z) isomer mediated by thiophenol and a radical source (Schwarz et al., J Org Chem 51:260-263 (1986)) followed by fractional crystallization.

Example 3

Ethyl (Z,Z)-11,13-Hexadecadienoate (3)

(Z,Z)-10,12-Pentadecadien-1-ol can be prepared using the appropriate starting materials using a previously reported reaction sequence (Sonnet, P. E., Heath, R. R., J Chem Ecol 6:221-228 (1980) The alcohol was converted to bromide (Scheme 1-3). The Grignard reagent of the bromide was prepared and quenched with excess diethylcarbonate (Whitmore F. C. and Loder, D. J., Ethyl, Naphthoate, In: Blott A H (ed) Organic Syntheses; John Wiley & Sons, New York, pp. 282-283 (1943)) to give the desired ester 3.

Example 4

(Z,Z)-11,13-Hexadecadien-1-yl Acetate (4)

Compound 4 was prepared by LAH reduction of the aldehyde (Z,Z)-1 followed by acylation of the alcohol with acetyl chloride (Scheme 1-4).

Example 5

(Z,Z,Z,Z,Z)-3,6,9,12,15-Tricosapentaene (5) and (Z,Z,Z,Z,Z)-3,6,9,12,15-Pentacosapentaene (6)

Commercially available methyl (Z,Z,Z,Z,Z)-5,8,11,14,17-eicosapentaenoate was reduced to the corresponding alcohol with Red-Al (Málek, J., Reduction by metal alkoxyaluminum hydrides, Part II, Carboxylic acids and derivatives, nitrogen compounds and sulfur compounds; In: Overman, L. (ed) Organic Reactions, John Wiley & Sons, New York, pp. 249 (1988)) (Scheme 1-5). The alcohol was then converted to bromide, which was coupled to either n-propyl or n-pentyl Grignard catalyzed by copper salts (Erdik, E., Tetrahedron Lett 40:641-657 (1984)) to give the 5 and 6 pentaenes, respectively.

Schemes 1-1 to 1-5

Scheme 1-1

Example 6

(Z)-11-Hexadecenal

(Z)-11-hexadecenal can be prepared by any number of published processes (Takikawa, H., et al. *Liebigs Annalen/ Recueil:*139-140 (1997); Gil, S., et al. *Synth Commun* 26:2329-2340 (1996); Kholbekov, O. Kh. And Abduvakhabov, A. A., *Uzbekskii Khimicheskii Zhurnal:*37-39 (1991); Trehan, I. R., et al. *Indian J Chem, Sec B* 29B:518-520 (1990)).

Example 7

(Z)-13-Hexadecenal (Z)-13-hexadecenal can be prepared by converting (Z)-9-dodecen-1-ol to the corresponding bromide via the mesylate using conventional methods (Jones, R. A., Quaternary Ammonium Salts, Academic Press, San Diego (2001)). The Grignard reagent of the bromide was then prepared and coupled with 1 equivalent of 1-bromo-3-chloropropane under copper catalysis (Erdik, E., *Tetrahedron Lett* 40:641-657 (1984)). The Grignard reagent of the resulting 1-chloro-(Z)-12-pentadecene is prepared and reacted with triethylorthoformate to give (Z)-13-hexadecenal diethyl acetal (De Wolf, H. R., Carboxylic Ortho Acid Derivatives, Academic Press. New York (1970)). Acidic hydrolysis gave the desired aldehyde (Greene, T. W. and Wuts, P. G. M., Protective Groups in Organic Synthesis, John Wiley & Sons. New York (1999))

Example 8

Field Experiments

Figure 3:
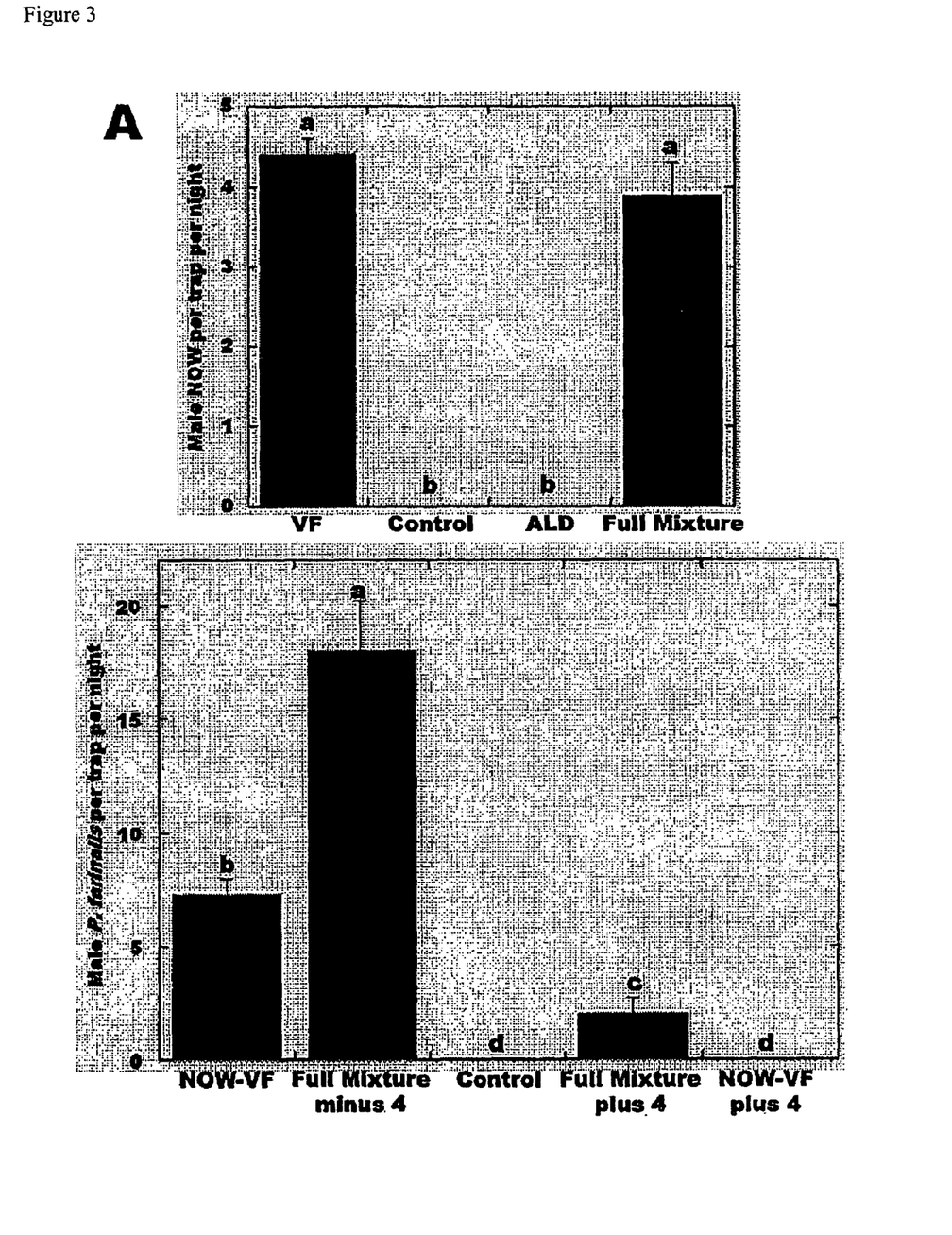

Experimental. Tests were conducted in almond and walnut plot fields in the UC Davis campus. Pheromone samples (0.5 mg) were formulated in rubber septa or in 12 mm diameter, 3 mm thick discs (made of ES fiber, Chisso Co. Ltd, Tokyo, Japan) and loaded into Pherocon 1C traps (Trece Inc., Salinas, Calif.). Three or five 1 to 3-day old virgin females were placed in fiberglass screen cages (Curtis, C. E. and Clark, J. D., *J Econ Entomol* 77:1057-1061 (1984) Curtis et al., *J Econ Entomol* 78:1425-1430 (1985)). Baited and control traps were placed at ca. 1.8 m height in randomized blocks with the intertrap distance of ca. 10 m. Capture data were transformed to log (x+0.5) and analyzed by ANOVA. In FIG. 3, treatments followed by the same letters are not significantly different at the 5% level in the Tukey-Kramer honestly significant difference. Means of captures are untransformed, and error bars show one standard error (SE).

Results. The ratio of the six constituents of the sex pheromone system of the navel orangeworm, analyzed by GC with three replicates of gland extracts, was (Z,Z)-11,13-hexadecadienal 100 (850±97 pg/female); ethyl palmitate, 14±1.3; ethyl (Z,Z)-11,13-hexadecadienoate, 4.8±1.4; (Z,Z)-11,13-hexadecadien-1-yl acetate, 4.9±1.2; (Z,Z,Z,Z,Z)-3,6,9,12,15-tricosapentaene, 14.9±2.4; and (Z,Z,Z,Z,Z)-3,6,9,12,15-pentacosapentaene, 17.1±4.3. Preliminary field tests in Davis showed that captures in traps baited with the full mixture of the pheromone system (0.5 mg) did not differ significantly from catches in traps baited with 1- to 3-day-old virgin females (FIG. 3A), whereas traps baited with the single pheromone constituent and control traps captured no moths in 3-wk period of tests.

In some locations, traps baited with virgin females of the navel orangeworm captured also males of the meal moth, *P. farinalis*. Interestingly, catches of the meal moth were significantly smaller when traps were baited with synthetic sample containing the full pheromone system. Tests with partial mixtures showed that removal of (Z,Z)-11,13-hexadecadien-1-yl acetate increased dramatically captures of male meal moth (FIG. 3B). This compound is a behavioral antagonist, which is not strong enough in the natural pheromone to completely repel the meal moth. This is supported by the complete lack of captures in traps baited with virgin females and boosted with a synthetic sample (0.5 mg/per device) of the acetate. In addition, GC-EAD experiments utilizing antennae of male meal moth captured in the pheromone traps confirmed that *P. farinalis* male do possess detectors tuned to (Z,Z)-11,13-hexadecadien-1-yl acetate.

Example 9

Plans and Procedures:

Insects:

A continuous colony of NOW was maintained at ARS-Parlier. This colony served several purposes: it supplied several thousand NOW female pupae for dissection and extraction, it provided male moths for use in coupled gas chromatography-electroantennogram studies, and it provided unmated females for trap baits for field tests. A second colony of NOW, more recently established from field-collected NOW, was used to produce males that performed well in wind tunnel experiments. A colony of *P. farinalis* was maintained on a modified lima bean diet to provide male moths for GC-electroantennogram assays, and females for extraction of pheromone. A second colony was established at ARS-Parlier to supply individuals for wind tunnel and field trials.

Identification and Synthesis of Previously Unidentified Compounds:

Pheromone glands were individually dissected out of >2,000 virgin female NOW, and the glands were extracted in ~250 microliters of pentane in composite batches of ~250-300 glands per extract. The extracts were screened by GC-EAD analysis to locate the compounds which elicited responses from male antennae (i.e., potential pheromone compounds). The extracts were then concentrated to ~10-20 microliters, and aliquots were analyzed on several GC columns with different polarity, by coupled GC-mass spectrometry, and by coupled GC-Fourier transform infrared spectrometry. A parallel set of studies was conducted with composite pheromone gland extracts prepared from *Pyralis* females. A subset of the extracts were also combined and fractionated by liquid chromatography, to provide samples for wind tunnel tests.

Having been identified, syntheses of each of the two new compounds were designed and carried out to provide ~100 mg of each of the two new compounds, to confirm the structures, and to provide material for the first laboratory and field trials.

Field Trials:

Field trials were carried out in Madera County using Pherocon 1C sticky traps baited with formulations of Z11, Z13-16:Ald plus the new compounds and other minor components previously identified from pheromone gland extracts. Three live unmated female moths held in a small screen cage inside traps were used as positive controls. Each treatment was replicated 5 times, and treatments were set out in a randomized design. Traps were checked at least once per week and lures were changed weekly if treatments were run longer.

Wind Tunnel Bioassays:

Flight responses of male NOW to different blends and doses of synthesized pheromone components were tested in the ARS wind tunnel. Males were 2-3 days old and were used during the last two hours of shotophase (dark cycle). The wind tunnel room was maintained at 23-26° C. with >35% relative humidity. NOW males were placed in individual aluminum-screen cages during their 1st or 2nd photophase and then held in an incubator until one hour prior to testing, when they were transferred from their dark incubator to the wind tunnel. The wind tunnel had a wind speed of 75 cm/s and light intensity was 1-2 lux (approximately full-moon light). After conditioning to ambient conditions in the wind tunnel for one hour, males were assayed individually to test compounds formulated on 1cm dia. filter paper disks. Information recorded included the number of males per trial that reached the pheromone source, the time to reach the pheromone source, and observations of the flight behavior (e.g., relatively straight flight; looping flight; veering out of the pheromone plume, etc.)

Results and Discussion:

Identification and Synthesis of Previously Unknown Compounds from Extracts of Pheromone Glands of Female NOW and *P. farinalis*.

Coupled GC-electroantennogram assays using *P. farinalis* males as test animals revealed trace amounts of a new compound ((Z,Z,Z,Z,Z)-3,6,9,12,15-tricosapentaene) in extracts of *P. farinalis* female pheromone glands that consistently elicited responses from the male antennae. Further GC-EAD trials using *P. farinalis* males to screen extracts of female NOW pheromone glands showed that the extracts also contained small amounts of (Z,Z,Z,Z,Z)-3,6,9,12,15-tricosapentaene. The NOW extract was then screened again by GC-EAD, this time using antennae of male NOW. The NOW antennae were found to give a much weaker response to (Z,Z,Z,Z,Z)-3,6,9,12,15-tricosapentaene than the *P. farinalis* antennae, and the response was only detectable at all in about half of the NOW antennal preparations tested, explaining why this response had been missed previously.

Having located the possible missing component, a series of composite extracts were analyzed by gas chromatography on multiple columns, and by coupled GC-mass spectrometry and GC-Fourier transform infrared spectrometry. A tentative structure for (Z,Z,Z,Z,Z)-3,6,9,12,15-tricosapentaene was proposed from the combination of bits of structural information from these various methods, and the structure was shown to be correct by synthesis of an authentic standard.

During the course of these analyses, an analog of (Z,Z,Z,Z,Z)-3,6,9,12,15-tricosapentaene was found in concentrated composite extracts of NOW pheromone glands. Given its structural similarity to the first compound, and the consequent likelihood that this compound ((Z,Z,Z,Z,Z)-3,6,9,12,15-pentacosapentaene) might also be biologically active, a second synthesis was carried out to provide a sample of (Z,Z,Z,Z,Z)-3,6,9,12,15-pentacosapentaene for testing as well.

Testing of the New Compounds in Laboratory Wind Tunnel Experiments.

Wind tunnel tests of male NOW responses to liquid chromatography-fractionated NOW pheromone gland extracts indicated that few males flew upwind to the fraction that contained only Z11,Z13-16:Ald and its isomers. However, as other fractions were added to the aldehyde fraction, it was found that one fraction consistently enhanced males' responsiveness. In particular, in response to the blend of these two fractions, males activated immediately, flew rapidly upwind, and contacted the odor source, similar to the response they exhibited to the crude, unfractionated extract. The response appeared to be further enhanced by a third fraction containing Z11,Z13-16:OH, the alcohol analog of the major component. Thus, these trials provided evidence that the pheromone consisted of multiple components with different chemical and physical properties.

Further wind tunnel testing was conducted with synthesized standards, using crude female extract as a positive control. Several points are clear. First, a high percentage of moths consistently flew upwind and contacted the source of crude pheromone extract (here and throughout all wind tunnel tests). Second, no test males responded to Z11,Z13-16:Ald as a single component. Furthermore, when synthetic Z11,Z13-16:Ald was added to crude female extract, male moths still responded well to this mixture, eliminating the possibility that the synthetic Z11,Z13-16:Ald contained inhibitory impurities. Third, blends of synthetic Z11,Z13-16:Ald with (Z,Z,Z,Z,Z)-3,6,9,12,15-tricosapentaene stimulated responses from male moths, and the data suggested that addition of Z11,Z13-16:OH to that blend further enhanced attraction. With this preliminary information suggesting the importance of both Z11,Z13-16:OH and (Z,Z,Z,Z,Z)-3,6,9,12,15-tricosapentaene as a starting point, field trials were conducted.

Subsequent wind tunnel tests were evaluated on quantitative as well as qualitative responses of NOW males to test formulations. All treatments were applied to 1 cm filter paper disks in at least 25 ul of hexane, to fully "wet" the paper surface, and at least 5 males were tested individually to each pheromone blend. Pheromone gland extracts (2 or 5 female equivalents) were tested to monitor male performance—throughout these tests all males tested to the pheromone gland extract flew upwind rapidly and contacted the source.

Once blends were found that elicited 30-40% upwind flight to the source, these blends were compared to extract, and then iteratively modified until higher source contact percentages were obtained (Table 1). Thus, various combinations of pheromone components were examined stepwise, focusing on partial or full mixtures of the six compounds that elicited EAG responses: Z11,Z13-16:Ald, Z11,Z13-16:OH, Z11,Z13-16:OH, 16:Ald, (Z,Z,Z,Z,Z)-3,6,9,12,15-tricosapentaene and (Z,Z,Z,Z,Z)-3,6,9,12,15-pentacosapentaene.

TABLE 1

Examples of wind tunnel tests (5 or more moths per treatment) of NOW male responses to synthetic pheromone components plus other test compounds.

| Treatment | Response Summary |
| --- | --- |
| 5 FE crude | 5 SC |
| 5 FE crude + 50 ng Ald | 5 SC |
| 5 FE crude + 100 ng Ald | 5 SC |
| 5 FE crude + 200 ng Ald | 4 SC, 1 up |
| 10 ng 6 cpd blend #1 | 2 SC, 3 up |
| 25 ng 6 cpd blend #1 | 5 SC, 1 upwind (5 cm FS), 4 up |
| 50 ng 6 cpd blend #1 | 6 SC, 1 up |
| 50 ng 6 cpd blend #1 | 8 SC, 3 upwind (2@10, & 50 cm FS), 1 up, 3 NR (15 flights) |
| 50 ng 6 cpd blend #2 | 3 SC, 1 upwind (200 cm FS), 7 up, 2 WF, 2 NR (15 flights) |
| 5 FE Crude | 15 SC |
| 25 ng 6 cpd blend #3 | 5 SC, 4 upwind (50, 70, 100, & 140 cm FS), 1 up |
| 25 ng 6 cpd blend #2 | 3 SC, 2 H@R, 5 up |
| 25 ng 6 cpd blend #1 | 7 SC, 1 up, 2 NR |
| 25 ng 5 cpd blend no OH | 3 SC, 1 upwind (45 cm FS), 3 H@R, 3 up |
| 25 ng 5 cpd blend no OH + 0.25 ng OH | 2 SC, 5 upwind (25, 35, 2@50, & 65 cm FS), 3 H@R |
| 10 ng 5 cpd blend no OH + 0.1 ng OH | 4 SC, 2 upwind (25, & 150 cm FS), 4 up |
| 10 ng 5 cpd blend no OH + 0.2 ng OH | 2 SC, 5 upwind (3, 5, 30, 45, & 50 cm FS), 1 H@R, 2 up |
| 10 ng 5 cpd blend no OH + 0.3 ng OH | 3 SC, 2 upwind (10 & 110 cm FS), 1 H@R, 2 up (8 flights) |
| 10 ng 5 cpd blend no OH | 1 SC, 5 upwind (1, 20, 45, 50, & 90 cm FS), 4 up |
| 10 ng 5 cpd blend no OH + 0.05 ng OH | 3 SC, 3 upwind (15, 35, & 85 cm FS), 3 hover, 1 NR |
| 10 ng 5 cpd blend no OH + | 4 SC, 5 upwind (35, 95, |

TABLE 1-continued

Examples of wind tunnel tests (5 or more moths per treatment) of NOW male responses to synthetic pheromone components plus other test compounds.

| Treatment | Response Summary |
|---|---|
| 0.1ng OH | 100, 150, & 160 cm FS), 1 H@R |
| 10 ng 5 cpd blend no OH | 3 SC, 1 upwind (160 cm FS), 2 up, 1 walk (7 flights) |
| 10 ng 5 cpd blend no OH + 0.,05 ng OH | 2 SC, 4 upwind (3, 15, 40, & 55 cm FS), 1 up (7 flights) |
| 10 ng 5 cpd blend no OH + 0.1 ng OH | 6 SC, I upwind (60 cm FS), 1 up (8 flights) |
| 10 ng 5 cpd blend no OH + 0.60 ng OH | 2 SC, 2 upwind (50 & 65 cm FS), 1 H@R |
| Above source + 0.1 Ong OH | 4 SC, 1 upwind (40 cm FS) (5 flights) |
| 10 ng 5 cpd blend no OH + 0.80 ng OH | 0 SC, 4 upwind (25, 30, 45, & 90 cm FS), 1 H@R |
| Above source + 0.1ng OH | 6 SC, 6 upwind (30, 70, 90, 95, 100, 105 cm FS), 1 H@R (13 flights) |
| 10 ng 4 cpd, +7% OH, +1% Ald | 9 SC, 1 up |
| 10 ng 4 cpd, +7% OH, +1% Ald | 6 SC, 1 upwind (20 cm FS), 3 up |
| 10 ng 4 cpd, +7% OH, +2.5% Ald | 4 SC, 5 upwind (2@10, 20, 45, & 60 cm FS), 1 walk |
| 20 ng 4 cpd, +7% OH, +1% Ald | 2 SC, 3 up |
| 10 ng 4 cpd, +7% OH, +1% Ald (again) | 4 SC, 2 upwind (60 & 100 cm FS), 1 H@R, 1 up (8 flights) |
| 10 ng 4 cpd, +7% OH, +1% Ald | 7 SC, I upwind (30 cm FS), 2 up |
| 10 ng 4 cpd, +7% OH, +1% Ald (again) | 7 SC, 1 upwind (140 cm FS), 2 up |
| 10 ng 4 cpd, +7% OH, +1.5% Aid | 6 SC, 2 upwind (60 & 110 cm FS), I H@R, 1 up |
| 10 ng 4 cpd, +7% OH, +1% Ald | 9 SC, 1 up |
| 10 ng 4 cpd, 7% OH, 1% Ald | 9 SC, 1 up |
| 10 ng 4 cpd, 7% OH, 1.5% Ald | 9 SC, 1 up |
| 10 ng 4 cpd, 7% OH, 2% Ald | 7 SC, 3 upwind (10, 35, & 125 cm FS) (10 total flights) |
| 10 ng 4 cpd, 7% OH, 0% Ald | 5 SC, 3 upwind (1, 10, & 110 cm FS), 1 up, I NR |
| 10 ng 3 cpd + 10%OH | 5 SC, 4 upwind (50, 55, 80, & 85 cm FS), 1 up |
| 10 ng 3 cpd + 7% OH | 9 SC, 1 upwind (5 cm FS) |
| 10 ng 3 cpd + 7% OH consistently elicited 70-90% source contact. This was the starting blend for field trials with wicks. | |

Key:
Line space - break between test days
FE = Female Equivalent(s)
SC = Source Contact
Ac = diene 16:acetate
OH = diene 16:alcohol
Ald = saturated 16:aldehyde
A = (Z,Z,Z,Z,Z)-3,6,9,12,15-tricosapentaene
B = (Z,Z,Z,Z,Z)-3,6,9,12,15-pentacosapentaene
FS = From Source
NR = No Response
H@R = Hover at Release
up = flew out of release cage but did not enter "pheromone" plume
Sources
6 cpd blend #1 = 100% diene aldehyde + 2% AC + 1.5% OH + 1% ALD + 258.42% A + 172.77% B
6 cpd blend #2 = 100% diene 16:Ald + 226% AC + 0.2% OH + 1.2% ALD + 5.35% A + 3.92% B
6 cpd blend #3 = 100% diene 16:Ald + 4.45% AC + 1.6% OH + 1.1% ALD + 8.42% A + 8.94% B
5 cpd blend no OH = 100% diene 16:Ald + 4.45% AC + 1.1% ALD + 7.6% A + 9.3% B
4 cpd = 100% diene aldehyde + 10.3% A + 12.5% B + 3.1% Ac
3 cpd blend = 100% diene aldehyde + 7.8% A + 11.5% B
All flights were to filter paper disk sources Testing of the New Compounds in Field Trials.

In the first field trial of Table 2, the best synthetic blend only attracted about 5% as les as virgin females. In the second trial of Table 2, the best blend of synthetics, consisting of a 100:4:333 blend of Z11,Z13-16:Ald with the corresponding alcohol and (Z,Z,Z,Z,Z)-3,6,9,12,15-tricosapentaene respectively, attracted 24% as many moths as the males, over a period of 5 days. A further series of seven sequential field trials with a wide variety of lure blends all suggested that Z11,Z13-16:OH and (Z,Z,Z,Z,Z)-3,6,9,12,15-tricosapentaene and (Z,Z,Z,Z,Z)-3,6,9,12,15-pentacosapentaene were components of the most active blend, because lures containing these components consistently out-performed lures with Z11,Z13-16:Ald as a single component (Table 2). However, the synthetic lures attracted fewer male moths than virgin females. This was determined to be linked to a combination of factors including when the lures were deployed, the type of lure, and the amount of time that the lures were exposed in the field.

TABLE 2

Summary of rationale behind field trials

| Trial # | Rationale |
|---|---|
| 1 | Test blends of Z11,Z13-16:Ald with increasing amounts of (Z,Z,Z,Z,Z)-3,6,9,12,15-tricosapentaene |
| 2 | Test fixed blends of Z11,Z13-16:Ald and Z11,Z13-16:OH with increasing amounts of (Z,Z,Z,Z,Z)-3,6,9,12,15-tricosapentaene |
| 3 | Test Z11,Z13-16:Ald with (Z,Z,Z,Z,Z)-3,6,9,12,15-tricosapentaene and (Z,Z,Z,Z,Z)-3,6,9,12,15-pentacosapentaene, and Z11,Z13-16:OH and Z11,Z13-16:Ac |
| 4 | Test Z11,Z13-16:Ald + multicomponent blend of possible other components with variable amounts of Z11,Z13-16:OH |
| 5 | Test different doses, reduced amount of Z11,Z13-16:Ald, and plastic capsule dispensers |
| 6 | Test Z11,Z13-16:Ald + variable doses of other components |
| 7 | Test effects of lures formulated on precleaned and noncleaned grey septa, and lures |
| 8 | Test cotton wick lures, deployed immediately after loading |
| 9 | Track decrease in activity of rubber septum lures with time |

While the field trials described above were being carried out, further wind tunnel trials were also being conducted in parallel, with the aim of determining which components of the blend were correlated with activity. Wind tunnel tests (above) indicated a possible blend ratio for field testing. The best blend, when formulated on cotton dental wicks, elicited good levels of activation and upwind flight, and ca. 70% source contact by male moths in the wind tunnel. The identical cotton wick lures were then tested in the field. In the first field trial with the wicks, they were loaded with the most active blend from the wind tunnel trials, but at 10 times the dose used in the wind tunnel. No NOW were captured with traps baited with wicks loaded with 10× or 100× the best tunnel blend after several nights and new baits, whereas female-baited traps in an adjacent block caught >25 males per night.

Figure 4:
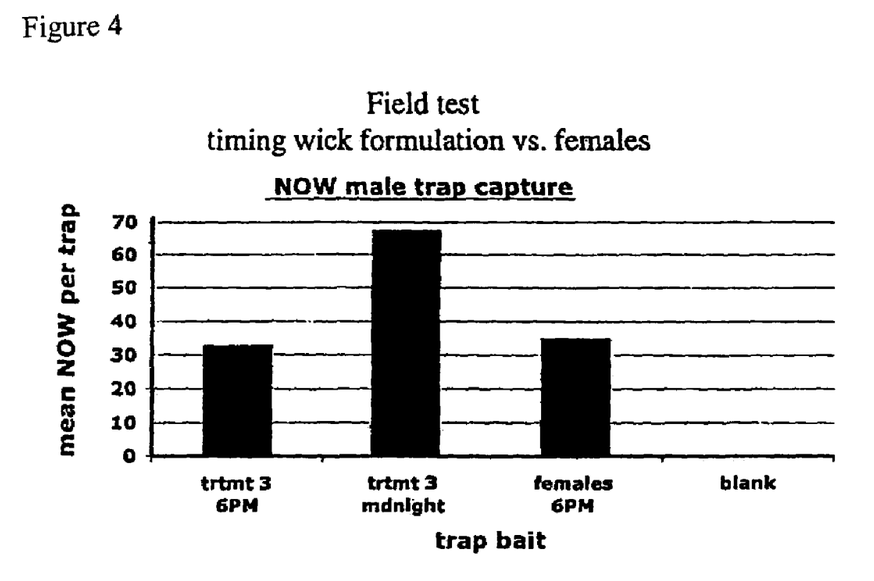
FIG. 4. NOW male trap capture in traps baited with synthetic pheromone on dental wicks vs. female-baited traps. Wicks were loaded with 10 ug Z11,Z13-16:Ald+7% Z11,Z13-16:OH+10% (Z,Z,Z,Z,Z)-3,6,9,12,15-tricosapentaene+15% (Z,Z,Z,Z,Z)-3,6,9,12,15-pentacosapentaene.

Pheromone compounds may have either evaporated too quickly from the cotton wick dispensers or deteriorated (no stabilizers were added to the formulation) in the heat prior to the males' responsive period during the last hours of darkness. Thus, again wicks were formulated with the same blend, but this time with lures placed in the traps at 6 PM in one subset, and at midnight in another subset, with female-baited traps also deployed at 6 PM. These wick-baited traps captured large numbers of NOW males, and the baits placed out at midnight captured more males than female-baited traps (FIG. 4). These results have several important implications. First, the fact that lures prepared from synthetic chemicals and used under "optimal" conditions attracted equal or greater numbers of male moths than traps baited with unmated females indicates that the blend ratio, and the chemistry of the blend components, is essentially correct, and that the synthetic chemicals do not contain any inhibitory impurities. Second, the fact that the effective longevity of the lures was short indicates that stabilization enhances lure longevity.

Figure 5:
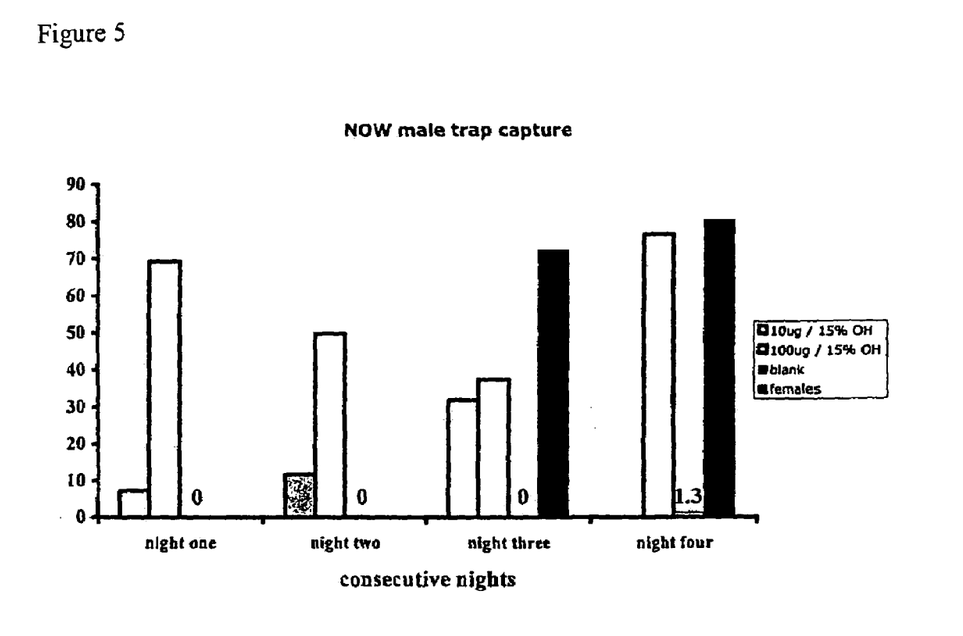
FIG. 5. NOW male trap capture in traps baited with synthetic pheromone on gray rubber septa vs. female-baited traps (no females were available the first 2 nights; 100 ug septa were replaced for the fourth night of testing). Septa were loaded with 10 ug or 100 ug Z11,Z13-16:Ald+15% Z11,Z13-16:OH+10% (Z,Z,Z,Z,Z)-3,6,9,12,15-tricosapentaene+15% (Z,Z,Z,Z,Z)-3,6,9,12,15-pentacosapentaene.

In a follow-up trial, septa were loaded with 10 ug and 100 ug doses of a similar blend of components (except that the alcohol component was raised to 15%); female-baited traps were not available until the third night. Traps were checked daily for 4 days; it was found that 100 ug baits captured high numbers of NOW males, and about 5 times more males than the 10 ug baits. Traps baited with fresh septa with 100 ug of the pheromone blend, on the fourth night, captured as many moths as female-baited traps (FIG. 5). Throughout these four days, blank traps captured zero or only a few moths. Further testing had to be suspended until October due to harvesting and spraying in the test blocks.

Figure 6:
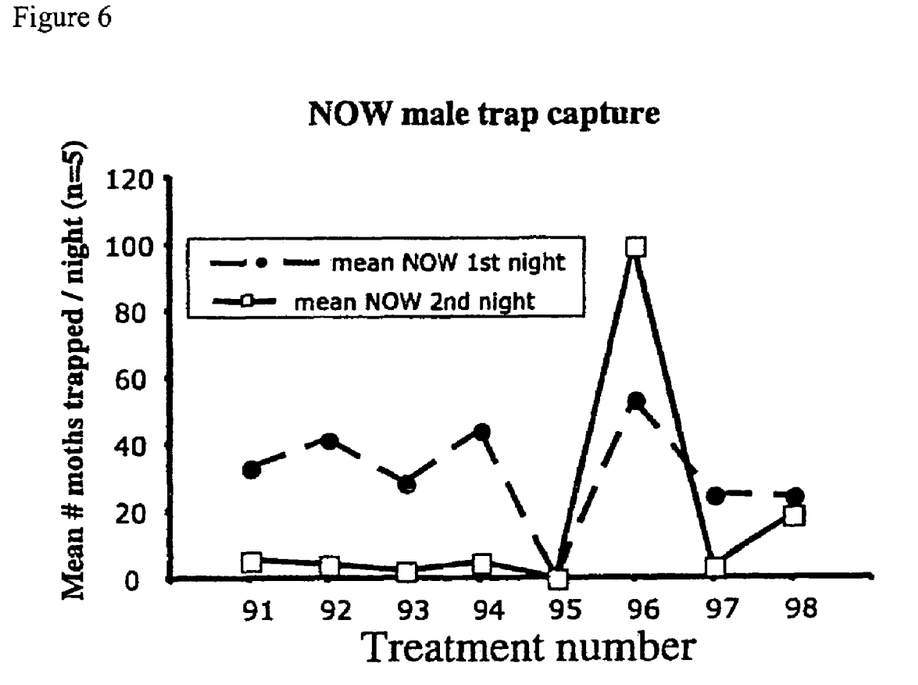
FIG. 6 NOW male trap capture on two consecutive nights in traps baited with synthetic pheromone on gray rubber septa vs. female-baited traps and blank traps. Septa were loaded with 10 ug or 100 ug Z11,Z13-16:Ald+15% Z11,Z13-16:OH+10% (Z,Z,Z,Z,Z)-3,6,9,12,15-tricosapentaene+15% (Z,Z,Z,Z,Z)-3,6,9,12,15-pentacosapentaene; treatment 95=unbaited traps, treatment 96=female-baited traps.

The above test was followed with trap baits formulated with the same 10 and 100 ug loadings on gray rubber septa. Two sets were formulated, one with stabilizers and one set without stabilizers. A third set was formulated on vacuum extracted septa without stabilizers added. On the first night of the test, 100 ug septa captured approximately as many NOW males as female-baited traps (FIG. 6). The other 100 ug septa also attracted high numbers of NOW. Traps were checked again a second night and at the end of one week; by the second night the overall trap counts for the septa were much lower than those from female baited traps (FIG. 6) and this trend continued to the end of the week. These results indicate that it is possible to reconstruct an effective pheromone attractant for male NOW.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A synthetic pheromone composition comprising Z,Z 11,13 hexadecadienal and (Z,Z,Z,Z,Z) 3,6,9,12,15 tricosapentaene.

2. The synthetic pheromone composition of claim 1, further comprising (Z,Z,Z,Z,Z) 3,6,9,12,15 pentacosapentaene.

3. The synthetic pheromone composition of claim 1, further comprising Z,Z 11,13 hexadecadien 1 ol.

4. The synthetic pheromone composition of claim 3, further comprising at least one member selected from the group consisting of Z,E 11,13 hexadecadienal, E,Z 11,13 hexadecadienal, Z 11 hexadecenal, hexadecanal, Z,E 11,13 hexadecadien 1 ol, Z 11-hexadecen-1-ol and methyl hexadecanoate.

5. The synthetic pheromone composition of claim 1, further comprising ethyl (Z,Z) 11,13 hexadecadienoate.

6. The synthetic pheromone composition of claim 5, further comprising (Z,Z,Z,Z,Z) 3,6,9,12,15 pentacosapentaene.

7. The synthetic pheromone composition of claim 5, further comprising at least one member selected from the group consisting of Z 13 hexadecenal and ethyl palmitate.

8. The synthetic pheromone composition of claim 1, further comprising at least one member selected from the group consisting of (Z,Z) 11,13 hexadecadien 1 yl acetate and hexadecyl acetate.

* * * * *

UNITED STATES PATENT AND TRADEMARK OFFICE
CERTIFICATE OF CORRECTION

PATENT NO. : 7,655,253 B2
APPLICATION NO. : 11/339088
DATED : February 2, 2010
INVENTOR(S) : Kuenen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 894 days.

Signed and Sealed this

Twenty-third Day of November, 2010

David J. Kappos
*Director of the United States Patent and Trademark Office*